United States Patent

Tomei

[11] Patent Number: 5,919,929
[45] Date of Patent: Jul. 6, 1999

[54] PROCESS FOR THE PREPARATION OF POLYTRIAZINE PRODUCTS CONTAINING 2, 2, 6, 6-TETRAMETHYL-4-PIPERIDYL GROUPS

[75] Inventor: Marco Tomei, Lucca, Italy

[73] Assignee: Ciba Specialty Chemicals Corporation, Tarrytown, N.Y.

[21] Appl. No.: 09/084,682

[22] Filed: May 26, 1998

[30] Foreign Application Priority Data

May 30, 1997 [IT] Italy .................................. MI97A1273

[51] Int. Cl.$^6$ .................................................. C07D 401/14
[52] U.S. Cl. .......................... 544/198; 544/209; 544/219
[58] Field of Search .................................... 544/198, 209, 544/219

[56] References Cited

U.S. PATENT DOCUMENTS

| | | | |
|---|---|---|---|
| 4,086,204 | 4/1978 | Cassandrini et al. ................... | 260/45.8 |
| 4,331,586 | 5/1982 | Hardy ........................................ | 525/186 |
| 4,335,242 | 6/1982 | Weizer et al. ............................ | 544/198 |
| 4,492,791 | 1/1985 | Orban et al. ............................. | 544/198 |
| 4,743,688 | 5/1988 | Minagawa ............................... | 544/113 |

FOREIGN PATENT DOCUMENTS

| | | |
|---|---|---|
| 0053775 | 11/1981 | European Pat. Off. . |
| 0357223 | 3/1990 | European Pat. Off. . |
| 0377324 | 7/1990 | European Pat. Off. . |
| 0782994 | 7/1997 | European Pat. Off. . |
| 9521157 | 8/1995 | WIPO . |

OTHER PUBLICATIONS

Chemical Abstract No. 97: 183468, 1982.

*Primary Examiner*—Yogendra N. Gupta
*Attorney, Agent, or Firm*—Luther A. R. Hall

[57] ABSTRACT

A process for the preparation of a product corresponding to the formula (I)

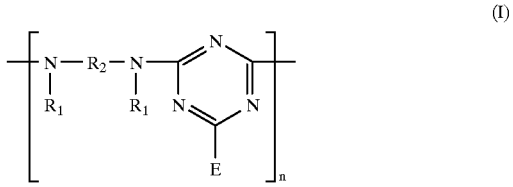

wherein n is a number from 2 to 50; the radicals $R_1$ are for example 2,2,6,6-tetramethyl-4-piperidyl, $R_2$ is for example hexamethylene and E is for example t-octylamino; which comprises a) reacting a compound of the formula (A)

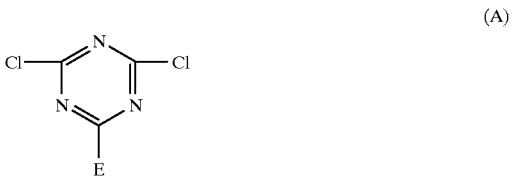

with a compound of the formula (B)

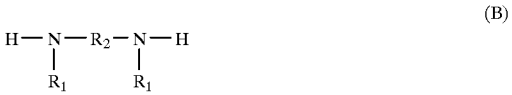

in a molar ratio of 1:1.7 to 1:4; and b) reacting the product obtained in a) with a compound of the formula (C)

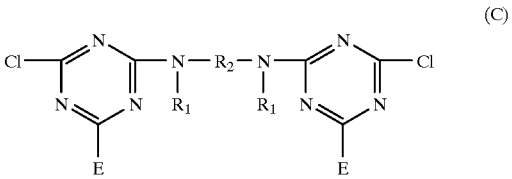

to obtain the product corresponding to the formula (I), the molar ratio of the compound of the formula (C) to the compound of the formula (A) being 2:1 to 1:5; the reactions a) and b) being carried out in an organic solvent, in the presence of an inorganic base and in an inert atmosphere.

14 Claims, No Drawings

PROCESS FOR THE PREPARATION OF POLYTRIAZINE PRODUCTS CONTAINING 2, 2, 6, 6-TETRAMETHYL-4-PIPERIDYL GROUPS

This invention relates to a process for the preparation of polytriazine products containing 2,2,6,6-tetramethyl-4-piperidyl groups. Said polytriazine products are useful as light stabilizers, heat stabilizers and oxidation stabilizers for organic materials, in particular synthetic polymers such as polyethylene and polypropylene.

The preparation of polytriazine products is described for example in U.S. Pat. Nos. 4,086,204, 4,331,586, 4,335,242, 4,492,791, EP-A-357 223 and EP-A-377 324.

In detail, this invention relates to a process for the preparation of a product corresponding to the formula (I)

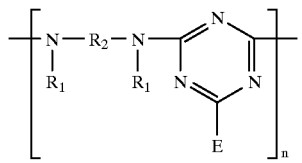

(I)

wherein n is a number from 2 to 50;

the radicals $R_1$ are independently of one another hydrogen, $C_1$–$C_8$alkyl, $C_5$–$C_{12}$cycloalkyl unsubstituted or substituted by 1, 2 or 3 $C_1$–$C_4$alkyl; or a group of the formula (II),

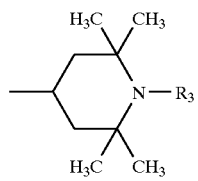

(II)

wherein $R_3$ is hydrogen, $C_1$–$C_8$alkyl, —O, —OH, —CH$_2$CN, $C_1$–$C_8$alkoxy, $C5$–$C_{12}$cycloalkoxy, $C_3$–$C_6$alkenyl, $C_7$–$C_9$phenylalkyl unsubstituted or substituted on the phenyl by 1, 2 or 3 $C_1$–$C_4$alkyl; or $C_1$–$C_8$acyl; with the proviso that at least one of the radicals $R_1$ is a group of the formula (II); $R_2$ is $C_2$–$C_{12}$alkylene, $C_4$–$C_{12}$alkenylene, $C_5$–$C_7$cycloalkylene, $C_5$–$C_7$cycloalkylene-di ($C_1$–$C_4$alkylene), $C_1$–$C_4$alkylenedi ($C_5$–$C_7$cycloalkylene), phenylenedi($C_1$–$C_4$alkylene) or $C_4$–$C_{12}$alkylene interrupted by 1,4-piperazinediyl, —O— or >N-$X_1$ with $X_1$ being $C_1$–$C_{12}$acyl or ($C_1$–$C_{12}$alkoxy) carbonyl or having one of the definitions of $R_5$ given below except hydrogen; or $R_2$ is a group of the formula (a) or (b);

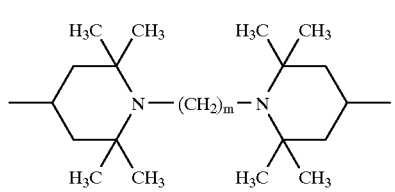

(a)

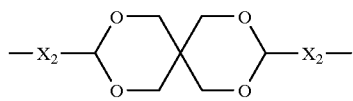

(b)

with m being 2 or 3; and the radicals $X_2$ being independently of one another $C_2$–$C_{12}$alkylene;

E is —OR$_4$, —N(R$_5$)(R$_6$) or a group of the formula (III);

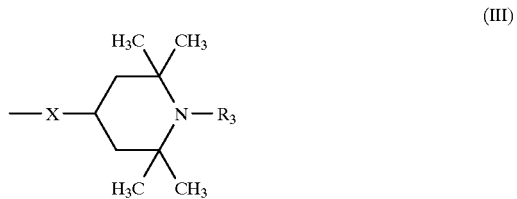

(III)

$R_4$, $R_5$ and $R_6$, which are identical or different, are hydrogen, $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by —OH, $C_1$–$C_8$alkoxy, di($C_1$–$C_4$alkyl) amino or a group of the formula (IV);

(IV)

with Y being —O—, —CH$_2$—, —CH$_2$CH$_2$— or >N—CH$_3$; or $R_4$ is additionally sodium or potassium; or —N(R$_5$)(R$_6$) is additionally a group of the formula (IV);

X is —O— or >N—R$_7$; and $R_7$ is hydrogen, $C_1$–C18alkyl, $C_3$–$C_{18}$ alkenyl, $C_5$–$C_{12}$cycloalkyl which is unsubstituted or substituted by 1, 2 or 3 $C_1$–$C_4$alkyl; $C_7$–$C_9$ phenylalkyl which is unsubstituted or substituted on the phenyl by 1, 2 or 3 $C_1$–$C_4$alkyl; tetrahydrofurfuryl, a group of the formula (II), or $C_2$–$C_4$alkyl which is substituted in the 2, 3 or 4 position by —OH, $C_1$–$C_8$alkoxy, di($C_1$–$C_4$alkyl)amino or a group of the formula (IV);

which comprises a) reacting a compound of the formula (A)

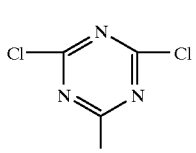

(A)

with a compound of the formula (B)

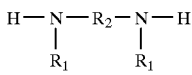
(B)

in a molar ratio of 1:1.7 to 1:4; and b) reacting the product obtained in a) with a compound of the formula (C)

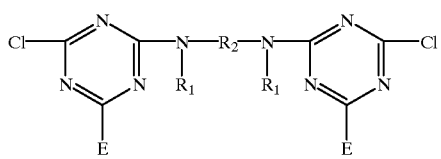
(C)

to obtain the product corresponding to the formula (I), the molar ratio of the compound of the formula (C) to the compound of the formula (A) being 2:1 to 1:5;

the reactions a) and b) being carried out in an organic solvent, in the presence of an inorganic base and in an inert atmosphere.

Examples of alkyl containing not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl. One of the preferred meanings of $R_3$ is $C_1$–$C_4$alkyl. One of the preferred meanings of $R_5$, $R_6$ and $R_7$ is $C_1$–$C_8$alkyl.

Examples of alkoxy containing not more than 18 carbon atoms are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. $C_6$–$C_{12}$Alkoxy, in particular heptoxy and octoxy, is one of the preferred meanings of $R_3$.

An example of $C_2$–$C_4$alkyl substituted by —OH is 2-hydroxyethyl.

Examples of $C_2$–$C_4$alkyl substituted by $C_1$–$C_8$alkoxy, preferably by $C_1$–$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$–$C_4$alkyl substituted by di($C_1$–$C_4$alkyl)amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

The group of the formula (IV) is preferably

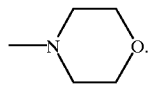

Preferred examples of $C_2$–$C_4$alkyl substituted by a group of the formula (IV) are groups of the formula

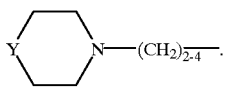

The group

is particularly preferred.

Examples of $C_5$–$C_{12}$cycloalkyl which is unsubstituted or substituted by 1, 2 or 3 $C_1$–$C_4$alkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Unsubstituted or substituted cyclohexyl is preferred.

Examples of $C_5$–$C_{12}$cycloalkoxy are cyclopentoxy, cyclohexoxy, cycloheptoxy, cyclooctoxy, cyclodecyloxy and cyclododecyloxy. $C_5$–$C_8$Cycloalkoxy, in particular cyclopentoxy and cyclohexoxy, is preferred.

Examples of alkenyl containing not more than 18 carbon atoms are allyl, 2-methylallyl, butenyl, hexenyl, undecenyl and octadecenyl. Alkenyls in which the carbon atom in the 1-position is saturated are preferred, and allyl is particularly preferred.

Examples of phenyl substituted by 1, 2 or 3 $C_1$–$C_4$alkyl or $C_1$–$C_4$alkoxy are methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of $C_7$–$C_9$ phenylalkyl which is unsubstituted or substituted on the phenyl by 1, 2 or 3 $C_1$–$C_4$alkyl are benzyl, methylbenzyl, dimethylbenzyl, trimethylbenzyl, t-butylbenzyl and 2-phenylethyl. Benzyl is preferred.

Examples of acyl (aliphatic, cycloaliphatic or aromatic) containing not more than 12 carbon atoms are formyl, acetyl, propionyl, butyryl, pentanoyl, hexanoyl, heptanoyl, octanoyl and benzoyl. $C_1$–$C_8$Alkanoyl and benzoyl are preferred. Acetyl is especially preferred.

Examples of alkoxycarbonyl wherein the alkoxy group contains not more than 12 carbon atoms are methoxycarbonyl, ethoxycarbonyl, propoxycarbonyl, butoxycarbonyl, pentoxycarbonyl, hexoxycarbonyl, heptoxycarbonyl, octoxycarbonyl, nonyloxycarbonyl, decyloxycarbonyl, undecyloxycarbonyl and dodecyloxycarbonyl.

Examples of alkylene containing not more than 12 carbon atoms are ethylene, propylene, trimethylene, tetramethylene, pentamethylene, hexamethylene, octamethylene, decamethylene and dodecamethylene. $R_2$ is for example $C_2$–$C_{10}$alkylene or $C_2$–$C_8$alkylene or $C_4$–$C_8$alkylene, in particular $C_2$–$C_6$alkylene, preferably hexamethylene.

An example of $C_4$–$C_{12}$alkenylene is 3-hexenylene.

An example of $C_5$–$C_7$cycloalkylene is cyclohexylene.

Examples of $C_4$–$C_{12}$alkylene interrupted by 1,4-piperazinediyl are

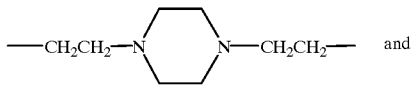 and

Examples of $C_4$–$C_{12}$alkylene interrupted by —O—, e.g. 1, 2 or 3 —O—, are 3-oxapentane-1,5-diyl, 4-oxaheptane- 1,7-diyl, 3,6-dioxaoctane-1,8-diyl, 4,7-dioxadecane-1,10-diyl, 4,9-dioxadodecane-1,12-diyl, 3,6,9-trioxaundecane-1,11-diyl and 4,7,10-trioxatridecane-1,13-diyl.

An example of $C_4$–$C_{12}$alkylene interrupted by >N-$X_1$ is

—$CH_2CH_2CH_2$—$N(X_1)$—$CH_2CH_2$—$N(X_1)$—$CH_2CH_2CH_2$—, in particular

—$CH_2CH_2CH_2$—$N(CH_3)$—$CH_2CH_2$—$N(CH_3)$—$CH_2CH_2CH_2$—.

An example of $C_5$–$C_7$cycloalkylenedi($C_1$–$C_4$alkylene) is methylene-cyclohexylene-methylene.

Examples of $C_1$–$C_4$alkylenedi($C_5$–$C_7$cycloalkylene) are cyclohexylene-methylene-cyclohexylene and cyclohexylene-isopropylidene-cyclohexylene.

An example of phenylenedi($C_1$–$C_4$alkylene) is methylene-phenylene-methylene.

n is preferably a number from 2 to 20, in particular 2 to 15.

The radicals $R_1$ are preferably a group of the formula (II).

According to a particular preferred embodiment of this invention the radicals $R_1$ are a group of the formula (II); and $R_2$ is $C_2$–$C_8$alkylene.

$R_3$ is preferably hydrogen, $C_1$–$C_4$alkyl, —OH, $C_6$–$C_{12}$alkoxy, $C_5$–$C_8$cycloalkoxy, allyl, benzyl or acetyl, in particular hydrogen or $C_1$–$C_4$alkyl. Hydrogen and methyl are especially preferred.

In the reaction a), the molar ratio of the compound of the formula (A) to the compound of the formula (B) is preferably 1:2 to 1:3, in particular 1:2 to 1:2.5.

The product obtained in the reaction a) may be described, for example, by the formula (A-B).

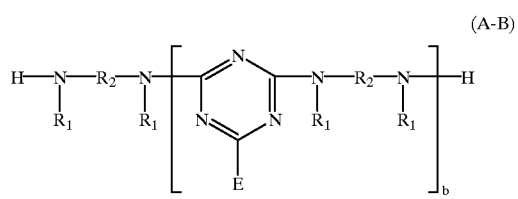

(A-B)

The variable b is a number from 1 to 8, preferably 1 to 6, in particular 1 to 4.

The product corresponding to the formula (A-B) is not a single specific compound but a product with a molecular weight distribution and, therefore, may also be described by a mixture containing at least 1) a monodispers*) compound of the formula (A-B-1),

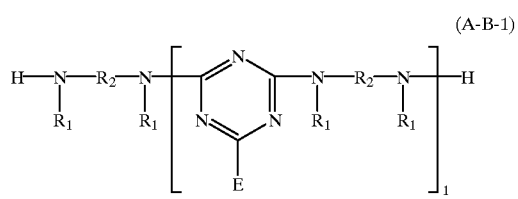

(A-B-1)

2) a monodispers compound of the formula (A-B-2) and

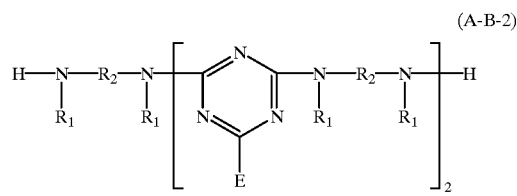

(A-B-2)

*) "monodispers" means that the compound has only one molecular weight and no molecular weight distribution.

3) a monodispers compound of the formula (A-B-3),

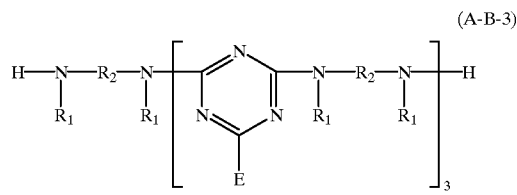

(A-B-3)

the compounds of the formulae (A-B-1), (A-B-2) and (A-B-3) differing only in the number of the repetitive units. Said compounds may be present in the mixture in an amount of, for example, 20 to 60 mol % (=(A-B-1)), 20 to 40 mol% (=(A-B-2)) and 20 to 30 mol % (=(A-B-3)), respectively.

The molar ratio of the reactant of the formula (C) used in the reaction b) as starting material to the compound of the formula (A) used in the reaction a) as starting material is preferably 1:1 to 1:5 or 1:2 to 1:5, in particular 1:3 to 1:4.

The reactions a) and b) are preferably carried out in a closed system under nitrogen. The temperature of the reaction a) is for example 60° to 190° C., preferably 70° to 180° C. and the temperature of the reaction b) is for example 70° to 200° C., preferably 80° to 190° C., in particular 100° to 180° C. When heating the reaction mixtures to the desired temperature, the pressure increases, since the reactions are carried out in a closed system. Because of the low boiling points of the organic solvents used, generally a pressure of 4 to 15 bars or 4 to 9 bars, in particular 6 to 8 bars is measured in the reactor.

The organic solvent used in the reactions a) and b) is preferably toluene, xylene, trimethylbenzene, isopropylbenzene, diisopropylbenzene or t-butylbenzene, in particular toluene, xylene or trimethylbenzene. Xylene is especially preferred.

The inorganic base used in the reactions a) and b) is preferably sodium hydroxide, potassium hydroxide, sodium carbonate or potassium carbonate, in particular sodium hydroxide or potassium hydroxide. Potassium hydroxide is especially preferred.

The reactions a) and b) are preferably carried out in the same organic solvent and in the presence of the same inorganic base.

After completion of the reaction a), it is advantageous to purify the reaction product by washing with water and filtering off the unsoluble by-products.

The starting material of the formula (A) can be prepared, for example, by reacting cyanuric chloride with a compound E-H in a stoichiometric ratio in the presence of an organic solvent and an inorganic base at a temperature of e.g. −20° to 100° C., preferably −10° to 60° C., in particular −10° to 30° C. It is appropriate to use for the preparation of the compound of the formula (A) the same solvent and the same inorganic base as in the above described reactions a) and b).

If desired, after the preparation of the starting material of the formula (A), the process according to this invention can follow immediately without isolation of the compound of the formula (A).

The starting materials of the formula (B) are known. In the case that they are not commercially available, they can be prepared analogously to known methods. For example, some starting materials of the formula (B) are described in WO-A-95/21 157 and U.S. Pat. No. 4,743,688.

The starting material of the formula (C) may be prepared, for example, by reaction of a compound of the formula (A) with a compound of the formula (B) in a stoichiometric ratio, preferably in the same organic solvent and in the presence of the same inorganic base as used in the reactions a) and b). The reaction is preferably carried out at a temperature of 40° to 80° C., preferably 60° to 80° C.

Examples of the terminal groups which saturate the free valences in the product corresponding to the formula (I) are given below.

The terminal group bonded to the diamino residue may be e.g. hydrogen or a group of the formula ($\alpha$).

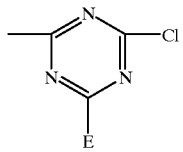

($\alpha$)

It is advantageous to replace the chloro radical being present in the group ($\alpha$) in a subsequent reaction, for example, by one of the radicals listed above for E.

When the terminal group is hydrogen, it is further possible to replace the hydrogen by e.g. $C_1$–$C_8$acyl, ($C_1$–$C_8$alkoxy) carbonyl, ($C_5$–$C_{12}$cycloalkoxy)carbonyl, ($C_1$–$C_8$alkyl) aminocarbonyl, ($C_5$–$C_{12}$cycloalkyl)aminocarbonyl, ($C_7$–$C_9$ phenylalkyl)aminocarbonyl, $C_1$–$C_8$alkyl, $C_5$–$C_{12}$cycloalkyl which is unsubstituted or substituted by 1, 2 or 3 $C_1$–$C_4$alkyl; $C_3$–$C_6$alkenyl, $C_7$–$C_9$ phenylalkyl which is unsubstituted or substituted on the phenyl by 1, 2 or 3 $C_1$–$C_4$alkyl; or —$CH_2CN$ in a subsequent reaction. Examples of most of these definitions are already given above.

A particularly preferred example of ($C_5$–$C_{12}$cycloalkoxy) carbonyl is cyclohexoxycarbonyl. ($C_5$–$C_7$cycloalkoxy) carbonyl is preferred.

Examples of ($C_1$–$C_8$alkyl)aminocarbonyl are methylaminocarbonyl, ethylaminocarbonyl, propylaminocarbonyl, butylaminocarbonyl, pentylaminocarbonyl, hexylaminocarbonyl, heptylaminocarbonyl and octylaminocarbonyl. ($C_1$–$C_4$alkyl) aminocarbonyl is preferred.

A particularly preferred example of ($C_5$–$C_{12}$cycloalkyl) aminocarbonyl is cyclohexylaminocarbonyl. ($C_5$–$C_7$cycloalkyl)aminocarbonyl is preferred.

A particularly preferred example of ($C_7$–$C_9$ phenylalkyl) aminocarbonyl is benzylaminocarbonyl.

The replacement of the chloro radical in the group ($\alpha$) may be carried out, for example, by reaction with a compound of the formula ($\beta$)

E-H  ($\beta$)

in an organic solvent and in the presence of an inorganic base at a temperature of e.g. 110° to 180° C. The molar ratio of the chloro radical to the compound of the formula ($\beta$) is for example 2:1.7 to 2:3. The radicals E in the final product obtained may be identical or different.

When the chloro radical is replaced by —OH, —ONa or —OK, the replacement is conveniently carried out by hydrolysis with $H_2O$ in an acidic medium, such as an aqueous hydrochloric solution, or with NaOH or KOH.

The replacement of the hydrogen end group may be carried out, for example, by reaction with a compound of the formula ($\gamma$) or ($\delta$)

A'—$Y_1$  ($\gamma$)

A"—NCO  ($\delta$)

wherein $Y_1$ is a leaving group, for example halogen, in particular chlorine;

A' is $C_1$–$C_8$acyl, ($C_1$–$C_8$alkoxy)carbonyl, ($C_5$–$C_{12}$cycloalkoxy)carbonyl, $C_1$–$C_8$alkyl, $C_5$–$C_{12}$cycloalkyl which is unsubstituted or substituted by 1, 2 or 3 $C_1$–$C_4$alkyl, $C_3$–$C_6$alkenyl, $C_7$–$C_9$phenylalkyl which is unsubstituted or substituted on the phenyl by 1, 2 or 3 $C_1$–$C_4$alkyl; or —$CH_2CN$; and A" is $C_1$–$C_8$alkyl, $C_5$–$C_{12}$cycloalkyl or $C_7$–$C_9$phenylalkyl; in about a stoichiometric ratio. The reaction is conveniently carried out in an organic solvent and in the presence of an inorganic base, e.g. that solvent and that inorganic base as already described above. When the reactant of the formula ($\delta$) is used, the replacement is carried out without any inorganic base.

When the reactant of the formula ($\gamma$) is used, the replacement may be carried out, for example, at a temperature of 60° to 180° C., preferably of 146° to 1600° C., if necessary in a closed vessel.

When the reactant of the formula ($\delta$) is used, the replacement may be carried out, for example, at a temperature of 0° to 60° C., preferably of 0° to 25° C.

The terminal group bonded to the triazinic residue of the product corresponding to the formula (I) is for example —Cl or a group of the formula ($\epsilon$).

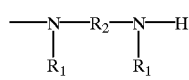

($\epsilon$)

The chloro radical and the hydrogen of the group ($\epsilon$) may be replaced, if desired, in the same manner as described above.

According to a preferred embodiment of this invention, the end group bonded to the diamino residue of the formula (I) is preferably hydrogen or a group of the formula ($\alpha$) and the end group bonded to the triazinic residue of the formula (I) is preferably —Cl or a group of the formula ($\epsilon$).

A preferred process is that wherein the radicals $R_1$ are independently of one another hydrogen, $C_1$–$C_4$alkyl, $C_5$–$C_8$cycloalkyl unsubstituted or substituted by methyl; or a group of the formula (II) with the proviso that at least one of the radicals $R_1$ is a group of the formula (II);

$R_2$ is $C_2$–$C_{12}$alkylene, $C_4$–$C_{12}$alkenylene, $C_5$–$C_7$cycloalkylene, $C_5$–$C_7$cycloalkylene-di($C_1$–$C_4$alkylene), $C_1$–$C_4$alkylenedi($C_5$–$C_7$cycloalkylene) or phenylenedi($C_1$–$C_4$alkylene);

$R_4$, $R_5$ and $R_6$ are independently of one another hydrogen, $C_1$–$C_{12}$alkyl, $C_5$–$C_7$cycloalkyl which is unsubstituted or substituted by 1, 2 or 3 $C_1$–$C_4$alkyl; $C_3$–$C_{12}$alkenyl, phenyl which is unsubstituted or substituted by 1, 2 or 3 $C_1$–$C_4$alkyl; benzyl which is unsubstituted or substituted on the phenyl by $C_1$–$C_4$alkyl; tetrahydrofurfuryl or $C_2$–$C_3$alkyl which is substituted in the 2 or 3 position by —OH, $C_1$–$C_4$alkoxy, di($C_1$–$C_4$alkyl)amino or a group of the formula (IV); or $R_4$ is additionally sodium or potassium; or —$N(R_5)(R_6)$ is additionally a group of the formula (IV); and $R_7$ is hydrogen, $C_1$–$C_{12}$alkyl, $C_5$–$C_7$cycloalkyl which is unsubstituted or substituted by 1, 2 or 3 $C_1$–$C_4$alkyl; benzyl which is unsubstituted or substituted on the phenyl by 1, 2 or 3 $C_1$–$C_4$alkyl; tetrahydrofurfuryl, a group of the formula (11) or $C_2$–$C_3$alkyl which is substituted in the 2 or 3 position by —OH, $C_1$–$C_4$alkoxy, di($C_1$–$C_4$alkyl)amino or a group of the formula (IV).

A particularly preferred process is that wherein
the radicals $R_1$ are independently of one another hydrogen, $C_1$–$C_4$alkyl, cyclohexyl or a group of the formula (II) with the proviso that at least one of the radicals $R_1$ is a group of the formula (II);

$R_2$ is $C_2$–$C_{10}$alkylene, cyclohexylene, methylene-cyclohexylene-methylene, cyclohexylene-methylene-cyclohexylene or methylene-phenylene-methylene;

$R_4$, $R_5$ and $R_6$ are independently of one another hydrogen, $C_1$–$C_8$alkyl, cyclohexyl which is unsubstituted or substituted by methyl; $C_3$–$C_8$alkenyl, phenyl which is unsubstituted or substituted by methyl; benzyl, tetrahydrofurfuryl or $C_2$–$C_3$alkyl substituted in the 2 or 3 position by —OH, $C_1$–$C_4$alkoxy, dimethylamino, diethylamino or 4-morpholinyl; or $R_4$ is additionally sodium or potassium; or —$N(R_5)(R_6)$ is additionally 4-morpholinyl; and $R_7$ is hydrogen, $C_1$–$C_8$alkyl, cyclohexyl which is unsubstituted or substituted by methyl;

benzyl, tetrahydrofurfuryl, a group of the formula (II) or $C_2$–$C_3$alkyl substituted in the 2 or 3 position by —OH, $C_1$–$C_4$alkoxy, dimethylamino, diethylamino or 4-morpholinyl.

A process of particular interest is that wherein
n is a number from 2 to 15;
the radicals $R_1$ are a group of the formula (II);
$R_2$ is $C_2$–$C_6$alkylene;
E is a group —$N(R_5)(R_6)$ or a group of the formula (III);
$R_5$ and $R_6$ are independently of one another hydrogen, $C_1$–$C_8$alkyl, 2-methoxyethyl or 2-ethoxyethyl; or —$N(R_5)(R_6)$ is additionally 4-morpholinyl;

X is >$NR_7$; and $R_7$ is $C_1$–$C_8$alkyl.

This invention is illustrated in more detail by the following examples. All percentages are by weight unless otherwise indicated.

EXAMPLE S (starting material)

Preparation of the Compound of the Formula

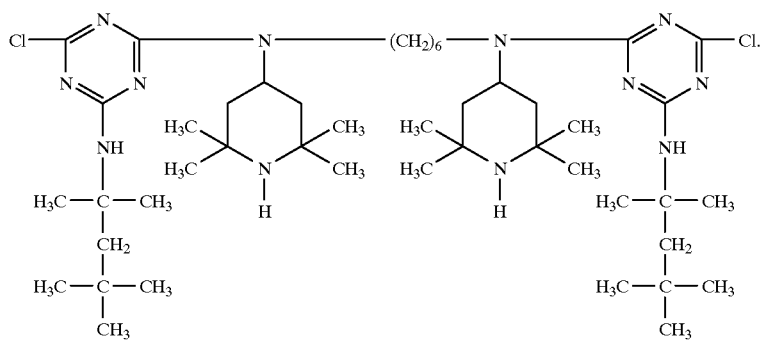

To a solution of 277.2 g (1.0 mole) of 2,4-dichloro-6-tert-octylamino-1,3,5-triazine in 500 ml of xylene, heated to 70° C, 194.3 g (0.5 moles) of N,N'-bis(2,2,6,6-tetramethyl-4-piperidyl)-1,6-hexanediamine and a solution of 67.3 g (1.2 moles) of potassium hydroxide in 68 ml of water are added, under stirring.

During the addition, the mixture is heated up to 80° C. and maintained at this temperature.

After the addition, the mixture is maintained at 80° C. for further one hour, under stirring. Then, the aqueous solution containing potassium chloride is decanted off and a xylenic suspension of the product is obtained. This suspension will be used without any isolation in the following Example 1.

In the structural formulae of Example 1, n and b indicate that there are repetitive units in the molecules and the products obtained are not monodispers.

Example 1

Preparation of the Product Corresponding to the Formula

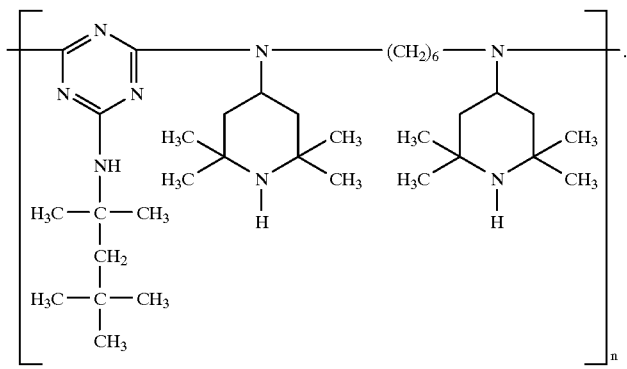

A) Preparation of the compound of the formula

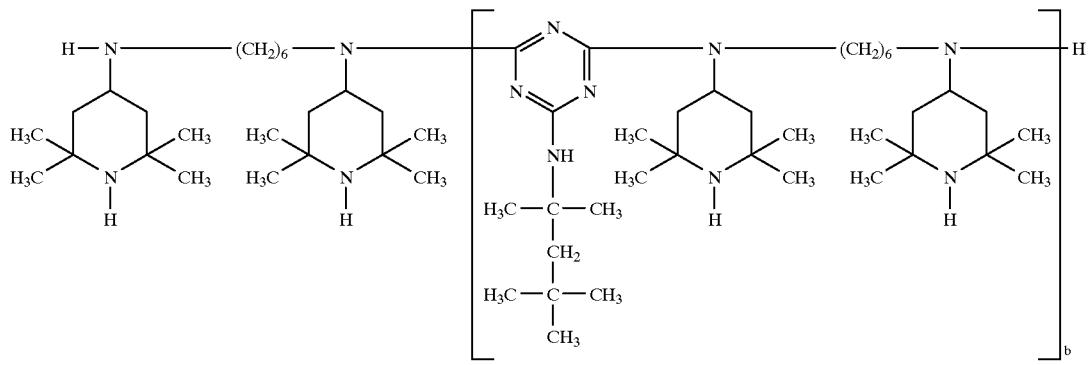

1.397 (3.54 moles) of N,N'-bis(2,2,6,6-tetramethyl-4-piperidyl)-1,6-hexanediamine, a solution of 203.1 g (3.62 moles) of potassium hydroxide in 203 ml of water and 492 g of water are loaded in a pressure vessel, equipped with a suitable stirrer.

Then, the mixture is heated up to 70° C. under stirring and a solution of 490.6 g (1.77 moles) of 2,4-dichloro-6-tert-octylamino-1,3,5-triazine in 980 ml of xylene are added.

Due to the exothermal reaction, the temperature rises up to 100° C. during the addition. Then, the vessel is closed and the mixture is heated to 180° C., and maintained at this temperature for 6 hours, under stirring. The internal pressure reaches 6 to 8 bars.

After cooling down to 80° C., the aqueous phase is separated off. The organic phase is filtered, treated with 420 ml of water to eliminate the unreacted N,N'-bis(2,2,6,6-tetramethyl-4-piperidyl)-1,6-hexanediamine as hydrate by precipitation, at a temperature of 45° to 20° C.

The precipitate is filtered, washed with 100 ml of xylene and the washing xylene is mixed with the organic solution.

About 300–350 ml of xylene are then distilled at 60° C./1 mbar and the xylenic solution of the product is used in B) without any isolation.

B) The xylenic suspension of Example S) and the xylenic solution according to A) are loaded in a pressure vessel equipped with a suitable stirrer. Under intense stirring, a solution of 639.5 g (11.4 moles) of potassium hydroxide in 640 ml of water and 900 ml of water are added.

The vessel is closed and the mixture is heated to 180° C. The internal pressure reaches 6 to 8 bars and the mixture is maintained at this pressure and at the indicated temperature for 6 hours, under stirring.

After cooling down to 80° C., the aqueous phase is separated off, the organic phase, after filtration, is washed with water and xylene is distilled off at 60° C./1 mbar. After drying in an oven in vacuo at 60° C./1 mbar, a white product with a melting range of 123° to 136° C. is obtained.

$\overline{Mn}$=2500 g/mol $\overline{Mw}$=5700 g/mol

Cl content: less than 0.05 % by weight.

I claim:

1. A process for the preparation of a product corresponding to the formula (I)

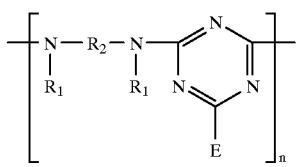

(I)

wherein n is a number from 2 to 50;

the radicals $R_1$ are independently of one another hydrogen, $C_1$–$C_8$alkyl, $C_5$–$C_{12}$cycloalkyl unsubstituted or substituted by 1, 2 or 3 $C_1$–$C_4$alkyl; or a group of the formula (II),

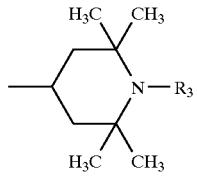

(II)

wherein $R_3$ is hydrogen, $C_1$–$C_{18}$alkyl, —O, —OH, —CH$_2$CN, $C_1$–$C_{18}$alkoxy, $C_5$–$C_{12}$cycloalkoxy, $C_3$–$C_6$alkenyl, $C_7$–$C_9$ phenylalkyl unsubstituted or substituted on the phenyl by 1, 2 or 3 $C_1$–$C_4$alkyl; or $C_1$–$C_8$acyl;

with the proviso that at least one of the radicals $R_1$ is a group of the formula (II);

$R_2$ is $C_2$–$C_{12}$alkylene, $C_4$–$C_{12}$alkenylene, $C_5$–$C_7$cycloalkylene, $C_5$–$C_7$cycloalkylene-di($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by 1,4-piperazinediyl, —O— or >N-$X_1$ with $X_1$ being $C_1$–$C_{12}$acyl or ($C_1$–$Cl_2$alkoxy)carbonyl or having one of the definitions of $R_5$ given below except hydrogen;

or $R_2$ is a group of the formula (a) or (b);

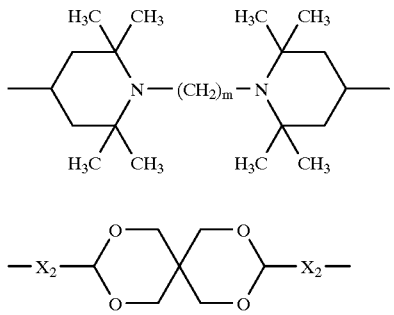

(a)

(b)

with m being 2 or 3; and the radicals $X_2$ being independently of one another $C_2$–$C_{12}$alkylene;

E is —OR$_4$, —N(R$_5$)(R$_6$) or a group of the formula (III);

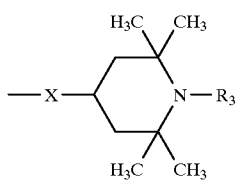

(III)

$R_4$, $R_5$ and $R_6$, which are identical or different, are hydrogen, $C_1$–$C_{18}$alkyl, $C_5$–$C_{12}$cycloalkyl which is unsubstituted or substituted by 1, 2 or 3 $C_1$–$C_4$alkyl; $C_3$–$C_{18}$alkenyl, phenyl which is unsubstituted or substituted by 1, 2 or 3 $C_1$–$C_4$alkyl or $C_1$–$C_4$alkoxy;

$C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by -OH, $C_1$–$C_8$alkoxy, di($C_1$–$C_4$alkyl)amino or a group of the formula (IV);

(IV)

with Y being —O—, –CH$_2$—, —CH$_2$CH$_2$— or >N—CH$_3$; or $R_4$ is additionally sodium or potassium; or —N(R$_5$)(R$_6$) is additionally a group of the formula (IV);

X is —O— or >N-R$_7$; and $R_7$ is hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (II), or $C_2$–$C_4$alkyl which is substituted in the 2, 3 or 4 position by -OH, $C_1$–$C_8$alkoxy, di($C_1$–$C_4$alkyl)amino or a group of the formula (IV);

which comprises a) reacting a compound of the formula (A)

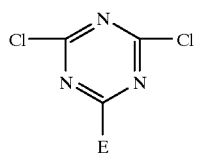

(A)

with a compound of the formula (B)

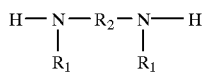

(B)

in a molar ratio of 1:1.7 to 1:4; and b) reacting the product obtained in a) with a compound of the formula (C)

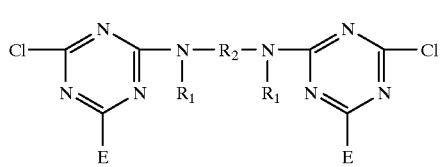

(C)

to obtain the product corresponding to the formula (I), the molar ratio of the compound of the formula (C) to the compound of the formula (A) being 2:1 to 1:5; the reactions a) and b) being carried out in an organic solvent, in the presence of an inorganic base and in an inert atmosphere.

2. A process according to claim 1 wherein the reactions a) and b) are carried out under a pressure of 4 to 15 bars.

3. A process according to claim 1 wherein the reaction a) is carried out at a temperature of 60 to 190° C. and the reaction b) is carried out at a temperature of 70 to 200° C.

4. A process according to claim 1 wherein the reactions a) and b) are carried out under nitrogen.

5. A process according to claim 1 wherein the organic solvent is toluene, xylene, trimethylbenzene, isopropylbenzene, diisopropylbenzene or t-butylbenzene.

6. A process according to claim 1 wherein the inorganic base is sodium hydroxide, potassium hydroxide, sodium carbonate or potassium carbonate.

7. A process according to claim 1 wherein the molar ratio of the compound of the formula (C) to the compound of the formula (A) is 1:3 to 1:4.

8. A process according to claim 1 wherein $R_3$ is hydrogen, $C_1$–$C_4$alkyl, —OH, $C_6$–$C_{12}$alkoxy, $C_5$–$C_8$cycloalkoxy, allyl, benzyl or acetyl.

9. A process according to claim 1 wherein $R_3$ is hydrogen or $C_1$–$C_4$alkyl.

10. A process according to claim 1 wherein the radicals $R_1$ are independently of one another hydrogen, $C_1$–$C_4$alkyl, $C_5$–$C_8$cycloalkyl unsubstituted or substituted by methyl; or a group of the formula (II) with the proviso that at least one of the radicals $R_1$ is a group of the formula (II);

$R_2$ is $C_2$–$C_{12}$alkylene, $C_4$–$C_{12}$alkenylene, $C_5$–$C_7$cycloalkylene, $C_5$–$C_7$cycloalkylene-di($C_1$–$C_4$alkylene), $C_1$–$C_4$alkylenedi($C_5$–$C_7$cycloalkylene) or phenylenedi($C_1$–$C_4$alkylene);

$R_4$, $R_5$ and R6 are independently of one another hydrogen, $C_1$–$C_{12}$alkyl, $C_5$–$C_7$cycloalkyl which is unsubstituted or substituted by 1, 2 or 3 $C_1$–$C_4$alkyl; $C_3$–$C_{12}$alkenyl, phenyl which is unsubstituted or substituted by 1, 2 or 3 $C_1$–$C_4$alkyl; benzyl which is unsubstituted or substituted on the phenyl by $C_1$–$C_4$alkyl; tetrahydrofurfuryl or $C_2$–$C_3$alkyl which is substituted in the 2 or 3 position by —OH, $C_1$–$C_4$alkoxy, di($C_1$–$C_4$alkyl)amino or a group of the formula (IV); or $R_4$ is additionally sodium or potassium; or —N($R_5$)($R_6$) is additionally a group of the formula (IV); and $R_7$ is hydrogen, $C_1$–$C_{12}$alkyl, $C_5$–$C_7$cycloalkyl which is unsubstituted or substituted by 1, 2 or 3 $C_1$–$C_4$alkyl; benzyl which is unsubstituted or substituted on the phenyl by 1, 2 or 3 $C_1$–$C_4$alkyl; tetrahydrofurfuryl, a group of the formula (II) or $C_2$–$C_3$alkyl which is substituted in the 2 or 3 position by —OH, $C_1$–$C_4$alkoxy, di($C_1$–$C_4$alkyl)amino or a group of the formula (IV).

11. A process according to claim 1 wherein the radicals $R_1$ are independently of one another hydrogen, $C_1$–$C_4$alkyl, cyclohexyl or a group of the formula (II) with the proviso that at least one of the radicals $R_1$ is a group of the formula (II);

$R_2$ is $C_2$–$C_{10}$alkylene, cyclohexylene, methylene-cyclohexylene-methylene, cyclohexylene-methylene-cyclohexylene or methylene-phenylene-methylene;

$R_4$, $R_5$ and $R_6$ are independently of one another hydrogen, $C_1$–$C_8$alkyl, cyclohexyl which is unsubstituted or substituted by methyl; $C_3$–$C_8$alkenyl, phenyl which is unsubstituted or substituted by methyl; benzyl, tetrahydrofurfuryl or $C_2$–$C_3$alkyl substituted in the 2 or 3 position by —OH, $C_1$–$C_4$alkoxy, dimethylamino, diethylamino or 4-morpholinyl; or $R_4$ is additionally sodium or potassium; or —N($R_5$)($R_6$) is additionally 4-morpholinyl; and $R_7$ is hydrogen, $C_1$–$C_8$alkyl, cyclohexyl which is unsubstituted or substituted by methyl; benzyl, tetrahydrofurfuryl, a group of the formula (11) or $C_2$–$C_3$alkyl substituted in the 2 or 3 position by —OH, $C_1$–$C_4$alkoxy, dimethylamino, diethylamino or 4-morpholinyl.

12. A process according to claim 1 wherein the radicals $R_1$ are a group of the formula (II); and $R_2$ is $C_2$–$C_8$alkylene.

13. A process according to claim 1 wherein n is a number from 2 to 20.

14. A process according to claim 1 wherein n is a number from 2 to 15;

the radicals R, are a group of the formula (II);

$R_2$ is $C_2$–$C_6$alkylene;

E is a group —N($R_5$)($R_6$) or a group of the formula (III);

$R_5$ and $R_6$ are independently of one another hydrogen, $C_1$–$C_8$alkyl, 2-methoxyethyl or 2-ethoxyethyl; or —N($R_5$)($R_6$) is additionally 4-morpholinyl;

X is >N$R_7$; and $R_7$ is $C_1$–$C_8$alkyl.

* * * * *